(12) United States Patent
Tu et al.

(10) Patent No.: US 7,790,188 B2
(45) Date of Patent: Sep. 7, 2010

(54) ANTIFUNGAL PROTEIN AND USAGE THEREOF

(75) Inventors: Ching-Yu Tu, Hsinchu (TW); Li-Ling Liaw, Hsinchu (TW)

(73) Assignee: Food Industry Research and Development Institute (TW)

( * ) Notice: Subject to any disclaimer, the term of this patent is extended or adjusted under 35 U.S.C. 154(b) by 478 days.

(21) Appl. No.: 11/646,352

(22) Filed: Dec. 27, 2006

(65) Prior Publication Data

US 2008/0161225 A1    Jul. 3, 2008

(51) Int. Cl.
- *A61K 39/00* (2006.01)
- *A61K 39/38* (2006.01)
- *A61K 38/00* (2006.01)
- *A01N 25/34* (2006.01)
- *A01N 63/04* (2006.01)
- *C07K 14/00* (2006.01)
- *C12P 7/66* (2006.01)

(52) U.S. Cl. .............. 424/274.1; 424/404; 424/184.1; 424/132.1; 424/278.1; 424/93.5; 530/300; 530/350; 435/133

(58) Field of Classification Search ................ None
See application file for complete search history.

(56) References Cited

U.S. PATENT DOCUMENTS

2004/0072325 A1*  4/2004  Anazawa et al. .......... 435/252.3
2006/0031962 A1*  2/2006  Altier et al. ................ 800/279

OTHER PUBLICATIONS

Bowie et al. (Science, 1990, 257:1306-1310).*
Carels, M. et al. "The Effect of Different Nitrogen Sources on Pigment Production and Sporulation of Monascus Species in Submerged, Shaken Culture" *Can. J. Microbiol.* (1977) vol. 23, No. 10, pp. 1360-1372.
Coca, M. et al. "Transgenic Rice Plants Expressing the Antifungal AFP Protein from *Aspergillus giganteus* Show Enhanced Resistance to the Rice Blast Fungus *Magnaporthe grisea*" *Plant Molecular Biology* (2004) vol. 54, pp. 245-259.
Endo, A. et al. "Monacolins J and L, New Inhibitors of Cholesterol Biosynthesis Produced by Monascus Ruber" *The Journal of Antibiotics* (1985) vol. 38, No. 3, pp. 420-422.
Galgoczy, L. et al. "Sensitivity of Different Zygomycetes to the Penicillium Chrysogenum Antifungal Protein (PAF)" *J. Basic Microbiol.* (2005) vol. 45, No. 2, pp. 136-141.
Hajjaj, H. et al. "Medium-Chain Fatty Acids Affect Citrinin Production in the Filamentous Fungus *Monascus ruber*" *Applied and Environmental Microbiology* (2000) vol. 66, No. 3, pp. 1120-1125.
Kaiserer, L. et al. "Characterization of the *Penicillium chrysogenum* Antifungal Protein PAF" *Arch Micobiol.* (2003) vol. 180, pp. 204-210.
Lee, D.G. et al. "Isolation and Characterization of a Novel Antifungal Peptide from *Aspergillus niger*" *Biochemical and Biophysical Research Communications* (1999) vol. 263, No. 3, pp. 646-651.
Liu, Y. et al. "A Chemically Modified Tetracycline (CMT-3) is a New Antifungal Agent" *Antimicrobial Agents Chemotherapy* (2002) vol. 46, No. 5, pp. 1447-1454.
Marx, F. et al. "Coning, Structural Organization and Regulation of Expression of the *Penicillium chrysogenum* Paf Gene Encoding an Abundantly Secreted Protein with Antifungal Activity" *Gene* (1995) vol. 167, pp. 167-171.
Ortoneda, M. et al. "In Vitro Interactions of Approved and Novel Drugs Against Paecilomyces Spp." *Antimicrobial Agents and Chemotherapy* (2004) vol. 48, No. 7, pp. 2727-2729.
Selitrennikoff, C.P. "Antifungal Proteins" *Applied and Environmental Microbiology* (2001)_vol. 67, No. 7, pp. 2883-2894.
Su, Y.C. et al. "Production of the Secondary Metabolites γ-Aminobutyric Acid and Monocolin K by *Monascus*" *J. Ind. Microbiol. Biotechnol.* (2003) vol. 30, No. 1, pp. 41-46.
Theis, T. et al. "New Insights into the Target Site and Mode of Action of the Antifungal Protein of *Aspergillus giganteus*" *Research in Microbiology* (2005) vol. 156, pp. 47-56.
Theis, T. et al. "The Antifungal Protein from *Aspergillus giganteus* Causes Membrane Permeabilization" *Antimicrobial Agents and Chemotherapy* (2003) vol. 47, No. 2, pp. 588-593.
Tsai, M.S. et al. "Purification and Characterization of an Acid Protease from Monascus Kaoliang" *Int. J. Peptide Protein Res.* (1978) vol. 12, pp. 293-302.
Tseng, Y.Y. et al. "Growth, Pigment Production and Protease Activity of *Monascus purpureus* as Affected by Salt, Sodium Nitrite, Polyphosphate and Various Sugars" *Journal of Applied Microbiology* (2000) vol. 88, No. 1, pp. 31-37.
Wnendt, S. et al. "Molecular Cloning, Sequence Analysis and Expression of the Gene Encoding an Antifungal-Protein from *Aspergillus giganteus*" *Current Genetics* (1994) vol. 25, pp. 519-523.
Moreno, A.B. et al. "Biotechnologically Relevant Enzymes and Proteins: Antifungal Mechanism of the *Aspergillus giganteus* AFP Against the Rice Blast fungus *Magnaporthe grisea*" *Appl. Microbiol. Biotechnol.* (2006) vol. 72, No. 5, pp. 883-895.
English abstract of CN 1687396 dated Oct. 26, 2005.

* cited by examiner

*Primary Examiner*—Robert B Mondesi
*Assistant Examiner*—Lakia J Tongue
(74) *Attorney, Agent, or Firm*—Ladas and Parry LLP (57) ABSTRACT

The present invention relates to an antifungal protein gene and cDNA sequence thereof, which is obtained by mining the whole genome sequences of *Monascus pilosus* BCRC 38072 and the unigene database. The gene can encode an antifungal protein MAFP1. A purified protein obtained from *M. pilosus* culture broth having molecular weight of about 7 kDa is identified as MAFP1 by N-terminal protein sequencing and comparative analysis. The purified MAFP1 protein can inhibit the growth of pathogens such as *Paecilomyces variotii* BCRC 33174 and *Helminthosporium panici* BCRC 35004. In addition, it is found by PCR test that the gene of this antifungal protein exists in other *Monascus* species such as *M. Barkeri, M. floridanus, M. lunisporas, M. pilosus, M. ruber* and the like. It is also been proved that the mafp1 gene and cDNA thereof in four *Monascus* strains, *M. pilosus* (BCRC 38072, BCRC 38093 and BCRC 31502) and *M. ruber* BCRC 31533, have the same DNA sequences.

3 Claims, 4 Drawing Sheets

MQFTKIAIFLFAAMGAVANPIAAESGDLDVRDVQLSKYGGECSLQHNTCT
Signal peptide         Propeptide            Mature protein

YLKGGKNQVVHCGSAANQKCKSDRHHCEYDEHHKTVNCQTPV

M. pilosus
A. giganteus
P. chrysogenum (B)

M. pilosus
A. giganteus
P. chrysogenum

SEQUENCE LISTING

```
<160> NUMBER OF SEQ ID NOS: 9

<210> SEQ ID NO 1
<211> LENGTH: 279
<212> TYPE: DNA
<213> ORGANISM: Monascus pilosus

<400> SEQUENCE: 1
atgcagttca ccaagattgc cattttcctc ttcgccgcaa tgggtgcagt tgccaacccc      60
attgcggccg agtcgggcga tctcgatgtc cgagatgtac agctcagtaa atatggagga     120
gagtgcagct tgcaacacaa cacctgcact tacctcaagg gtggaaagaa ccaagtagtc     180
cactgcggtt cggctgccaa ccagaagtgc aaatctgatc gccaccactg tgaatacgat     240
gagcaccaca agacggtcaa ctgccagacc ccggtttaa                            279

<210> SEQ ID NO 2
<211> LENGTH: 92
<212> TYPE: PRT
<213> ORGANISM: Monascus pilosus

<400> SEQUENCE: 2

Met Gln Phe Thr Lys Ile Ala Ile Phe Leu Phe Ala Ala Met Gly Ala
1               5                   10                  15

Val Ala Asn Pro Ile Ala Ala Glu Ser Gly Asp Leu Asp Val Arg Asp
                20                  25                  30

Val Gln Leu Ser Lys Tyr Gly Gly Glu Cys Ser Leu Gln His Asn Thr
            35                  40                  45

Cys Thr Tyr Leu Lys Gly Gly Lys Asn Gln Val Val His Cys Gly Ser
        50                  55                  60

Ala Ala Asn Gln Lys Cys Lys Ser Asp Arg His His Cys Glu Tyr Asp
65                  70                  75                  80

Glu His His Lys Thr Val Asn Cys Gln Thr Pro Val
                85                  90

<210> SEQ ID NO 3
<211> LENGTH: 58
<212> TYPE: PRT
<213> ORGANISM: Monascus pilosus

<400> SEQUENCE: 3

Leu Ser Lys Tyr Gly Gly Glu Cys Ser Leu Gln His Asn Thr Cys Thr
1               5                   10                  15

Tyr Leu Lys Gly Gly Lys Asn Gln Val Val His Cys Gly Ser Ala Ala
                20                  25                  30

Asn Gln Lys Cys Lys Ser Asp Arg His His Cys Glu Tyr Asp Glu His
            35                  40                  45

His Lys Thr Val Asn Cys Gln Thr Pro Val
        50                  55
```

-continued

```
<210> SEQ ID NO 4
<211> LENGTH: 409
<212> TYPE: DNA
<213> ORGANISM: Monascus pilosus

<400> SEQUENCE: 4
atgcagttca ccaagattgc catttcctc ttcgccgcaa tgggtgcagt tgccaacccc      60
attgcggccg agtcgggcga tctcgatgtc cgagatgtac agctcagtaa atatggagga    120
gtaagttttt cttatgagat gtgatgtttc tatggagata cactgactt ttctgattca     180 atgtacagga gtgcagcttg caacacaaca cctgcactta cctcaagggt ggaaagaacc    240
aagtagtcca ctgcggttcg gctgccaacc agaaggtaca taacgattcg attccggacc    300
aacttatttg ttctcatcat ctaatcctca tctacagtgc aaatctgatc gccaccactg    360
tgaatacgat gagcaccaca agacggtcaa ctgccagacc ccggtttaa               409

<210> SEQ ID NO 5
<211> LENGTH: 15
<212> TYPE: PRT
<213> ORGANISM: Monascus pilosus

<400> SEQUENCE: 5

Leu Ser Lys Tyr Gly Gly Glu Cys Ser Leu Gln His Asn Thr Cys
1               5                   10                  15

<210> SEQ ID NO 6
<211> LENGTH: 16
<212> TYPE: DNA
<213> ORGANISM: Monascus pilosus

<400> SEQUENCE: 6
atgcagttca ccaaga                                                     16

<210> SEQ ID NO 7
<211> LENGTH: 21
<212> TYPE: DNA
<213> ORGANISM: Monascus pilosus

<400> SEQUENCE: 7
ttaaaccggg gtctggcagt t                                               21

<210> SEQ ID NO 8
<211> LENGTH: 14
<212> TYPE: DNA
<213> ORGANISM: Monascus pilosus

<400> SEQUENCE: 8
caaccccatt gcgg                                                       14

<210> SEQ ID NO 9
<211> LENGTH: 18
<212> TYPE: DNA
<213> ORGANISM: Monascus pilosus

<400> SEQUENCE: 9
cagtaaatat ggaggaga                                                   18
```

ANTIFUNGAL PROTEIN AND USAGE THEREOF

FIELD OF THE INVENTION

The present invention relates to an antifungal protein and the usage thereof. Methods for the preparation of such protein are provided. The present invention also relates to sequences of antifungal protein and DNA encoding the said protein sequences, vector containing said DNA sequences, cells transformed with said DNA sequences, and methods for treating and/or controlling fungal diseases.

BACKGROUND OF THE INVENTION

It is known that more than 200 animal fungal pathogens and more than 30 common plant fungal pathogens can make great impact on human health and economics. At present, the major drugs for controlling human fungal pathogens are the small molecules such as polyenes, azoles, fluconazole, amphotericin B, and the like. With the increasing number of drug abuse, the situation of drug resistance of the fungal strains becomes more and more severe. There is an urgent need of developing new antifungal drugs (see Selitrennikoff, C. P., 2001, Antigungal proteins, *Appl. Environ. Microbiol.* 67, 2883-2894, and Liu Y., Ryan, M. E., Lee, H. M., Simon, S., Tortora, G., Lauzon, C., Leung, M. K. and Golub, L. M., 2002, A chemically modified tetracycline (CMT-3) is a new antifungal agent. *Antimicrob. Agents Chemother.* 46, 1447-1454).

Plants, bacteria, fungi, insects, birds and mammals are all known to be able to produce antifungal proteins (see Kaiserer, L., Oberparieiter, C., Weiler-Görz, R. Burgstaller, W., Leiter, E. and Marx, F., 2003, Characterization of the *Penicillium chrysogenum* antifungal protein PAF. *Arch Microbiol.* 180, 204-210). Although these proteins have different amino acid sequence and quaternary structure, their properties of low molecular weight, highly basic and high cysteine content are the major molecular characteristics for most antifungal proteins (see Selitrennikoff et al., 2001).

There are a few antifungal proteins from filamentous fungi been studied, for example AFP protein from *Aspergillus giganteus* (see Wnendt, S., Ulbrich, N. and Stahl, U., 1990, Cloning and nucleotide sequence of a cDNA encoding the antifungal-protein of *Aspergillus giganteus* and preliminary characterization of the native gene. *Nucleic Acids Res.* 18, 3987, Wnendt, S., Ulbrich, N. and Stahl, U., 1994, Molecular cloning, sequence analysis and expression of the gene encoding an antifungal protein from *Aspergillus giganteus. Curr. Genet.* 25, 519-523, Theis, t., Marx, F., Salvenmoser, W., Stahl, U. and Meyer, V., 2005, New insights into the target site and mode of action of the antifungal protein of *Aspergillus giganteus. Res. Microbilol.* 156, 47-56, and Theis, T., Wedde, M., Meyer, V. and Stahl, U., 2003, The antifungal protein from *Aspergillus giganteus* causes membrane permeabilization. *Antimicrob. Agents Chemother.* 47, 588-593), PAF protein from *Penicillium chrysogenum* (see Marx, F., Hass, H., Reindl, M., Stoffler, G., Lottspeich, F. and Redl B., 1995, Cloning, structural organization and regulation of expression of the *Penicillium chrysogenum* paf gene encoding an abundantly secreted protein with antifungal activity. *Gene* 167, 167-171, and Kaiserer et al., 2003), and Anafp protein from *Aspergillus niger* (see Lee, G. D., Shin, S. Y., Maeng, C. Y., Jin, Z. Z., Kim, K. L. and Hahm, K S., 1999, Isolation and characterization of a novel antifungal peptide from *Aspergillus niger. Biochem. Biophys. Res. Commun.* 263, 646-651). The aforementioned antifungal proteins are all secretary proteins, and they can inhibit the growth of a wide range of fungi, but do not influence bacteria and yeasts. These antifungal proteins have similar molecular characteristics, but there are only 42% sequence similarities between the amino acid sequences of the antifungal proteins PAF and AFP (see Kaiserer et al., 2003). These fungus-derived antifungal proteins mainly inhibit fungi of genus *Aspergillus* and *Fusarium* spp. (see Theis et al., 2003, and Kaiserer et al., 2003). PAF protein can further inhibit human and animal fungal pathoghes such as *Abaidia* spp., *Mortierella* spp., *Rhizomucor* spp. and *Rhizopus* spp. These proteins are useful not only as biologically controlling agents for plant fungal pathogen, but also as potential human and animal antifungal drugs (see GalgÓczy, L., Papp. T., Letter, É. Marx, F., Pócsi, I. And Vágvölgyi, C., 2005, Sensitivity of different Zygomycetes to the *Penicillium chrysogenum* antifungal protein (PAF). *J. Basic microbial.* 45, 136-141). In addition, it has been reported that the resistance of rice to the rice blast pathogen *Magnaporthe grisea* can be enhanced by transfecting the cDNA of AFP protein from *Aspergillus giganteus* into the rice, and therefore the AFP protein can be used in the prevention of rice blast (see Coca, M., Bortolotti, C., Rufat, M., Penas, G., Eritja, R., Tharreau, D., del Pozo A, M., Messeguer, J. and San Segundo, B., 2004, Transgenic rice plants expressing the antifungal AFP protein from *Aspergillus giganteus* show enhanced resistance to the rice blast fungus *Magnaporthe grisea. Plant Mol. Biol.* 54, 245-259, and Moreno, A. B., Martinez Del Pozo, A. and San Segundo B. 2006, Biotechnologically relevant enzymes and proteins: Antifungal mechanism of the *Aspergillus giganteus* AFP against the rice blast fungus *Magnaporthe grisea. Appl. Microbiol. Biotechnol.* 72(5):883-895).

*Paecilomyces variotii* and *P. lilacinus* are the most ubiquitous species of the genus *Paecilomyces* and also the most frequently involved in human infections. Endophthalmitis and endocarditis are two of the most common infections produced by *P.s variotii* and *P. lilacinus* respectively, and have a very bad prognosis. The failure rate of the standard treatment for the infections is about 40%. The future approaches for the treatments will be using combination therapy or developing new classes of antifungal agents (see Ortoneda, M., Capilla, J., Pastor, F. J., Pujol, I., Yustes, C., Serena, C. and Guarro, J. (2004) In vitro interaction of approved and novel drugs against *Paecilomyces* spp. *Antimicrob. Agents Chemother.* 48, 2727-2729). *Helminthosporium panici* is the pathogen of plant ring spot disease. It is an important topic to use biological molecular technique to effectively prevent the fungal infection and decrease the losses caused by the fungal diseases to human health, economical crops and animal husbandry.

*Monascus* species are important traditional fungi for fermentation in eastern Asia, and are used in the manufacture of fermented products such as alcoholics, fermented red rice (anka), soybean curd (sufu), soybean sauce, and the like. In addition, *Monascus* species can produce various metabolites and enzymes, such as monacolin K (see Endo, A., Hasumi, K. and Negishi, S. (1985) Monacolins J and L, new inhibitors of cholesterol biosynthesis produced by *Monascus rubber. J. Antibiot. (Tokyo)* 38(3):420-2), citrinin (see Hajjaj, H., klaebe, A., Goma, G., Blanc, P. J., Barbier, E. and Francois, J. (2000) Medium-chain fatty acids affect citrinin production in the filamentous fungus *Monascus rubber, Appl. Environ. Microbiol.* 66(3):1120-5), GABA (see Su, Y. C., Wang, J. J., Lin, T. T. and Pan, T. M. (2003) Production of the secondary metabolites gamma-aminobutyric acid and monacolin K by *Monascus. J. Ind. Microbiol. Biotechnol.* 30(1):41-6), red and yellow pigments (see Carels, M. and Shepherd, D. (1977) The effect of different nitrogen sources on pigment production and sporulation of *Monascus* species in submerged, shaken culture. *Can. J. Microbiol.* 23(10): 1360-72, and Tseng, Y. Y., Chen, M. t. and Lin, C. F. (2000) Growth, pigment production and protease activity of *Monascus purpureus* as affected by salt, sodium nitrite, polyphosphate and various sugars. *J. Appl. Microbiol.* 88(1):31-7), and protease (see Tsai, M. S., Hseu, T. H. and Shen, Y. S. (1978) Purification and characterization of an acid protease from *Monascus kaoliang. Int. J. Protein Res.* 12, 293-302), and thus have high potential in the drug developments and the application of industrial enzymes. Among the applications, citrinin is known to have the activity to inhibit the growth of bacteria. However, there is no literature publication regarding the activity of *Monascus* species to inhibit the growth of fungi. Our earlier whole genome sequencing and decoding project of *Monascus* mined a possible antifungal protein gene, and therefore it is suggest that *Monascus* species may possess antifungal activities.

SUMMARY OF THE INVENTION

One of the purposes of the present invention is to provide an isolated and purified antifungal protein MAFP1 obtained from a *Monascus* species. Preferably, the *Monascus* species is selected from the group consisting of *Monascus barkeris, Monascus floridanus, Monascus lunisporas, Monascus pilosus* and *Monascus ruber*. More preferably, *Monascus* species is selected from the group consisting of *Monascus barkeris* BCRC 33309=ATCC 16966, *Monascus floridanus* BCRC 33310=IMI 282587, *Monascus lunisporas* BCRC 33640=ATCC 204397, *Monascus pilosus* BCRC 38072 (preserved in Bioresource Collection and Research Center (BCRC), Food Industry Research and Development Institute (FIRDI), 331 Shih-Pin Road, Hsinchu, 300 Taiwan R.O.C.), BCRC 38093 (preserved in BCRC, FIRDI) and BCRC 31502=ATCC 16363, *Monascus ruber* BCRC 31523=ATCC 16378, BCRC 31533=ATCC 16246, BCRC 31534=ATCC 16366, BCRC 31535=ATCC 18199, BCRC 33314=ATCC 16371 and BCRC 33323=ATCC 18199.

Another purpose of the present invention is to provide an isolated and purified polynucleotide comprising a nucleotide sequence encoding the antifungal protein MAFP1.

Another purpose of the present invention is to provide a recombinant vector nucleotide sequence encoding the antifungal protein MAFP1.

Another purpose of the present invention is to provide a recombinant host cell comprising the recombinant vector of this invention.

Another purpose of the present invention is to provide a composition comprising the antifungal protein of this invention and a suitable carrier, wherein the protein is provided in an amount sufficient to provide protection against fungal disease.

Another purpose of the present invention is to provide a method of controlling plant fungus comprising applying to a plant the antifungal protein of this invention in an amount sufficient to provide protection against fungal diseases.

Another purpose of the present invention is to provide a transgenic organism having incorporated into its genome a transgene that encodes the antifungal protein of this invention.

Another purpose of the present invention is to provide a method of treating fungal diseases in a patient comprising administering the patient the antifungal protein of this invention in an amount sufficient to provide protection against fungal disease.

Still another purpose of the present invention is to provide an isolated and purified primer pair, which can amplify nucleotides encoding the antifungal protein of this invention.

A further purpose of the present invention is to provide a PCR assay kit, comprising the primer pair of this invention The present invention is described in detail in the following sections. Other characterizations, purposes and advantages of the present invention can be easily found in the detailed descriptions and claims of the invention.

DETAILED DESCRIPTION OF THE INVENTION

The present invention features a novel gene, hereinafter designated mafp1, in *Monascus* species and characterized by having similarities to genes encoding the antifungal proteins AFP in *Aspergillus giganteus* and gene encoding PAF in *Penicillium chrysogenum*. It is found that the protein encoded by the novel gene, hereinafter designated MAFP1, has antifungal activity and is useful in treating and/or controlling fungal diseases.

Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated and purified protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the isolated protein is associated in nature, (6) is operably associated with (by covalent or noncovalent interaction) with a polypeptide with which it is not associated in nature, or (7) does not occur in nature. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use. An isolated and purified protein may also be rendered substantially free of naturally associated components by isolation, using protein purification techniques well known in the art.

The term "antifungal protein" means protein having antifungal properties, e.g., that inhibits the growth of fungal cells, kills fungal cells, or disrupts or retards stages of the fungal life cycle such as spore germination, sporulation, and mating.

The term "amino acid sequence" means an amino acid sequence of a naturally occurring protein molecule. "Amino acid sequence" and like terms, such as "polypeptide" or "protein" are not meant to limit the amino acid sequence to the complete, native amino acid sequence associated with the recited protein molecule. Amino acid sequence includes an oligopeptide, peptide, polypeptide, or protein sequence, and fragments or portions thereof, and to naturally occurring or synthetic molecules The term "biologically functional equivalent" refers to equivalents with respect to the antifungal proteins of the present invention that contain a sequence or moiety exhibiting sequence similarity to the novel peptides of the present invention such as MAFP1, and that exhibit the same or similar functional properties as that of the polypeptides disclosed herein, including antifungal activity. For instance, the biologically functional equivalent of the antifungal protein of the invention may have some alterations in the amino acid sequence that is different from, but essentially identical to, the amino acid sequence of the protein, and has essentially identical properties of the protein as described herein, even if in less or greater degree.

The terms "isolated and purified polynucleotide" referred to herein means that a subject polynucleotide (1) is not associated (covalently or noncovalently) with all or a portion of other polynucleotides with which the subject polynucleotide is associated in nature, (2) is associated with a molecule with which it is not associated in nature, or (3) does not occur in nature associated with any other polynucleotides. Such a polynucleotide may be genomic DNA, cDNA, mRNA or other RNA, of synthetic origin, or any combination thereof. Preferably, the isolated and purified polynucleotide of the invention comprises a single coding region. Although the polynucleotide includes a single coding region, it can contain additional nucleotides that do not detrimentally affect the function of the polynucleotide. For example, the 5' and 3' untranslated regions may contain variable numbers of nucleotides. Preferably, additional nucleotides are outside the single coding region.

The term "nucleotide sequence" means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modification such as bromouridine and inosine derivatives, ribose modification such as 2',3'-dideoxyribose, and internucleotide linkage modifications such as phosphorodiselenoate, phosphoroanilothioate, phosphoranilidate and phosphoroamidate, and the like. A nucleotide sequence of the invention can include a label, including a radiolabel, a fluorescent label, a hapten or an antigenic label for detection assays.

The term "vector" means any molecule (e.g., nucleic acid, plasmid, episome, or virus) used to transfer coding information to a host cell. The term also includes a "recombinant vector," "expression vector" or "expression construct." The term "expression vector" or "expression construct" refers to a vector that is suitable for transformation of a host cell and contains nucleotide sequences that direct and/or control (in conjunction with the host cell) expression of one or more heterologous coding regions operatively linked thereto. An expression construct may include, but is not limited to, sequences that affect or control transcription, translation, and RNA splicing, if introns are present, of a coding region operatively linked thereto. Preferred vectors are those capable of autonomous replication and expression of nucleic acids which they are linked.

The term "host cell" means a cell that has been transformed, or is capable of being transformed, with a nucleic acid sequence and thereby expresses a selected gene of interest. The term includes the progeny of the parent cell, whether or not the progeny is identical in morphology or in genetic mark-up to the original parent cell, so long as the selected gene is present.

The term "transformation" refers to a change in a cell's genetic characteristics, and a cell has been transformed when it has been modified to contain new DNA. For example, a cell is transformed where it is genetically modified from its native state by transfect, transduction, or other techniques.

The term "transgenic organism" refers to any organism in which one or more, and preferably essentially all, of the cells of the organism introduced with an exogenous gene. The gene is introduced into the cell, directly or indirectly by introduction into a precursor of the cell, by way of deliberate genetic manipulation, such as by microinjection or by infection with a recombinant vector. The term genetic manipulation includes not only classical cross-breeding, or in vitro fertilization, but also the introduction of a recombinant DNA molecule, which may be integrated within a chromosome or may be extrachromosomally replicating DNA. A transgenic animal includes an animal, or the organ, tissue or cell derived from the transgenic animal. A transgenic plant includes a plant, progeny thereof, seeds from the transgenic plant, or cells derived from a transformed plant cell or protoplast.

The term "identity" refers to a relationship between the sequences of two or more polypeptide molecules or two or more nucleic acid molecules, as determined by comparing the sequences thereof. "Identity" measures the percentage of identical matches between the smaller of two or more sequence.

The term "similarity is used in the art with regard to a related concept; in contrast to "identity," however, "similarity" refers to a measure of relatedness that includes both identical matches and conservative substitution matches.

Unless otherwise required by context, singular terms shall include pluralities and plural terms shall include the singular.

*Monascus* Antifungal Protein and Gene Thereof

One object of the invention is to provide an isolated and purified antifungal protein from *Monascus* species. Another object of the invention is to provide the isolated and purified polynucleotide comprising a nucleotide sequence encoding the antifungal protein. The *Monascus* antifungal protein and gene encoding the antifungal protein were discovered through mining of the *Monascus* whole genome database and comparative analysis.

Figure 1:
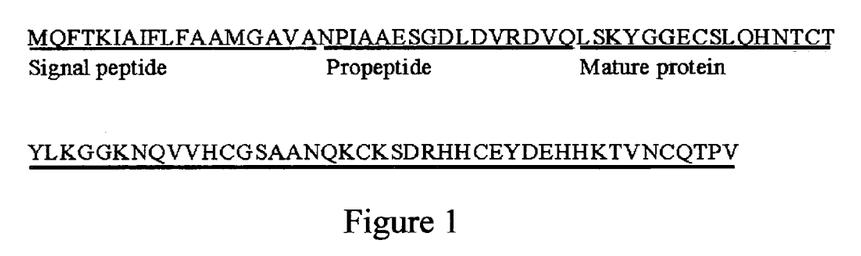
FIG. 1 shows amino acid sequence of *Monascus* antifungal protein MAFP1. The signal peptide is shown in blue; the propeptide is shown in purple; and the mature protein is shown in red.

The amino acid sequences of antifungal proteins AFP of *Aspergillus giganteus* (accession No. emb|CAA37523.1|) and PAF of *Penicillium chrysogenum* (accession No. gb|AAA92718.1|) were compared with the sequences of the unigene database from whole genome sequence database of *M. pilosus* BCRC 38072 (the Food Industry Research and Development Institute (FIRDI)'s in-house database) using tblastn. The BLAST program (including blastp, blastn, blastx, tblastn, tblastx and like programs) is publicly available from the National Center for Biotechnology Information (NCBI) and other sources (BLAST Manual, Altschul et. al., NCB/NLM/NIH Bethesda, Md. 20894). A unigene contig having about 30% similarity to the protein sequences of AFP and PAF was obtained and analyzed with Vector NTI (Infor-Max) software for open reading frame (ORF) prediction. A 279 base pair cDNA (SEQ ID NO: 1) was identified by ORF prediction, which can be translated into a protein consisting of 92 amino acids (SEQ ID NO: 2). The antifungal protein was named MAFP1. The sequence as shown in SEQ ID NO: 2 was found to have a signal peptide (positions 1-18), a propeptide (positions 19-34) and a mature protein (position 35-92) (see FIG. 1). It is suggested that this protein can be secreted out of the *Monascus* cell.

Figure 2:
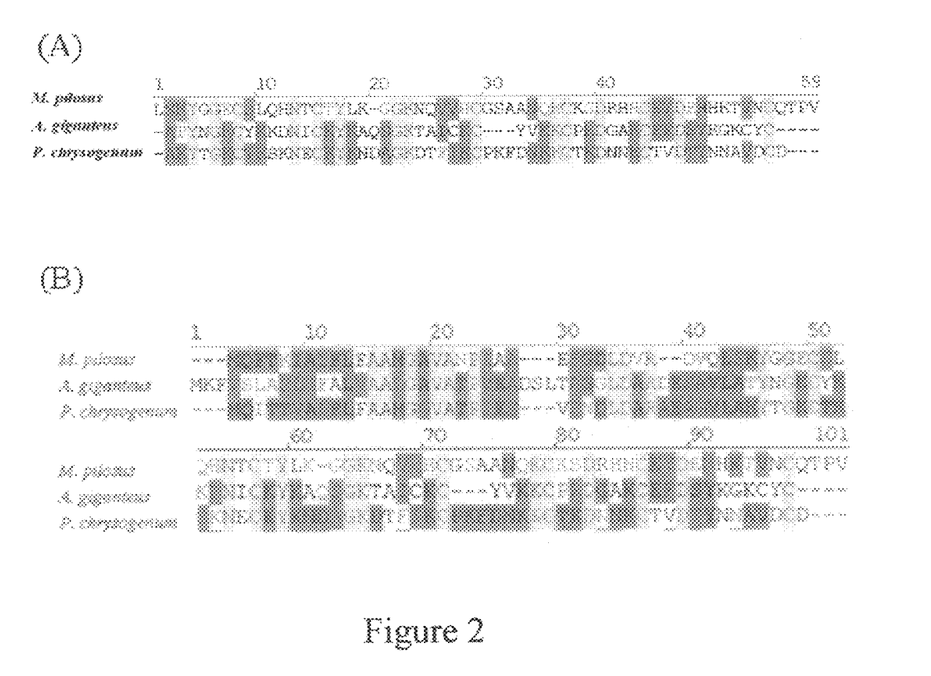
FIG. 2 shows sequence alignment of (A) mature regions (B) and full length of antifungal protein MAFP1 of *M. pilosus*, AFP protein of *A. giganteus*, and PAF protein of *P. chrysogenus*. The yellow region represents identical amino acid residues of the three protein sequences; the blue region represents identical amino acid residues of two protein sequences; and the green region represents amino acid residues having similar properties.

The sequence as shown in SEQ ID NO: 1 was compared with the *Monascus* whole genome database using blastn, and a genomic DNA sequence for the antifungal protein was obtained (SEQ ID NO: 4), named mafp1 gene. The sequences as shown in SEQ ID NO: 1 and SEQ ID NO: 4 were compared with NCBI DNA database using blastn, and the sequence as shown in SEQ ID NO: 2 was compared with NCBI and Swiss-Prot protein databases using tblastn to identify the published sequences similar to the DNA and protein sequences of MAFP1. The Alignment program of Vector NTI software was used for aligning the amino acid sequences of MAFP1 (SEQ ID NO: 2), AFP of *Aspergillus giganteus* (accession No. emb|CAA37523.1|) and PAF of *Penicillium chrysogenum* (accession No. gb|AAA92718.1|) to find the highly conserved sequence (AAXGXVAXP) of the amino acid sequences (see FIG. 2(B)). It is found that there is a highly conserved region within the regions of signal peptide and propeptide. The mature protein sequence (SEQ ID NO: 3) of MAFP1 has 29% and 31% similarities to the amino acid sequence of AFP of *Aspergillus giganteus* and PAF of *Penicillium chrysogenum*, respectively. The six cysteines at positions 8, 15, 28, 36, 43 and 54 of the mature MAFP1 sequence are the highly conserved residues of antifungal protein of fungal origin. There is no similar DNA sequences to the cDNA of MAFP1 (SEQ ID NO: 1) and the genomic DNA sequence (mafp1, SEQ ID NO: 4) were found in DNA sequences in NCBI nr database by blastn comparison. Thus, it can be concluded that MAFP1 is a novel protein and mafp1 is a novel gene.

Peptides, polypeptides, and proteins biologically functionally equivalent to the antifungal protein of the invention are contemplated as within the scope of the invention and include amino acid sequences containing conservative amino acid changes in the fundamental sequence of the antifungal protein. In such amino acid sequences, one or more amino acids in the fundamental sequence are substituted with another amino acid(s), the charge and polarity of which are similar to that of the native amino acid, i.e., a conservative amino acid substitution, resulting in a silent change.

Substitutes for an amino acid within the fundamental polypeptide sequence can be selected from other members of the class to which the naturally occurring amino acid belongs.

Amino acids can be divided into the following four groups: (1) acidic amino acids, (2) basic amino acids, (3) neutral polar amino acids, and (4) neutral nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental protein sequence can be made by substituting one amino acid within one of these groups with another amino acid within the same group. Biologically functional equivalents of the antifungal protein can have 20 or fewer conservative amino acid changes, more preferably 10 or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of the antifungal protein.

The biologically functional equivalent peptides, polypeptides, and proteins contemplated herein should therefore possess about 80% or greater sequence similarity, preferably about 85% or greater sequence similarity, and most preferably about 90% or greater sequence similarity, to the sequence of, or corresponding moiety within, the fundamental amino acid sequence of antifungal protein of the invention.

Although the antifungal polypeptide of the present invention preferably comprises the amino acid sequence shown in SEQ ID NO: 2, or biologically functional equivalents thereof, fragments and variants of these sequences possessing the same or similar antifungal activity as that of this antifungal polypeptide are also encompassed by the present invention. Thus, contiguous sequences of 8 or more amino acids in SEQ ID NO: 2 may exhibit such activity.

Fragments of SEQ ID NO: 2 can be truncated forms wherein one or more amino acids are deleted from the N-terminal end, C-terminal end, the middle of the polypeptide, or combinations thereof. These fragments can be naturally occurring or synthetic mutants of SEQ ID NO: 2 and should retain the antifungal activity of SEQ ID NO: 2.

Variants of SEQ ID NO: 2 include forms wherein one or more amino acids have been inserted into the natural or synthetic sequence. These variants can also be naturally occurring or synthetic mutants of SEQ ID NO: 2 and should retain the antifungal activity of SEQ ID NO: 2.

Combinations of the foregoing, i.e., forms of the antifungal protein containing both amino acid deletions and additions, are also encompassed by the present invention. Amino acid substitutions can also be present therein as well.

The fragments and variants of SEQ ID NO: 2 encompassed by the present invention should preferably possess about 70% or greater sequence similarity, more preferably about 80% or greater sequence similarity, and most preferably about 90% or greater sequence similarity, to the corresponding regions of SEQ ID NO: 2.

Other biologically functional equivalent forms of the antifungal protein of the invention useful in the present invention include conjugates of the polypeptides, or biologically functional equivalents thereof as described above, with other peptides, polypeptides, or proteins, forming fusion products therewith exhibiting the same, similar, or greater antifungal activity as compared with that of the antifungal protein of the invention.

Biologically functional equivalents also include peptides, polypeptides, and proteins that react with, i.e., specifically bind to, antibodies raised against the antifungal protein of the invention and that exhibit the same or similar antifungal activity, including both monoclonal The method for producing the biologically functional equivalent of a polypeptide or a protein include any suitable method know in the art, such as direct chemical synthesis or synthesis in heterologous biological systems such as microbial, plant, and animal systems; tissue cultures; cell cultures; or in vitro translation systems. Methods for altering the amino acid sequences are well known in the art such as genetic engineering techniques, e.g., site-directed mutagenesis to modify the nucleotide acid sequences or the amino acid sequences and expression of recombinant proteins.

The present invention includes not only the DNA sequence shown in SEQ ID NO: 1 or 4 but also biologically functional equivalent nucleotide sequences. The phrase "biologically functional equivalent nucleotide sequences" denotes DNAs and RNAs, including genomic DNA, plasmid DNA, cDNA, synthetic DNA, and mRNA nucleotide sequences, that encode peptides, polypeptides, and proteins exhibiting the same or similar antifungal activity as that of SEQ ID NO: 2, i.e., when introduced into host cells in a functionally operable manner so that they are expressed, they produce peptides, polypeptides, or proteins exhibiting antifungal activity at a level sufficient to confer resistance to fungal pathogens upon such cells.

Biologically functional equivalent nucleotide sequences of the present invention include nucleotide sequences encoding conservative amino acid changes within the fundamental antifungal protein sequence, producing silent changes therein. Such nucleotide sequences contain corresponding base substitutions compared to nucleotide sequences encoding wild-type antifungal proteins, such as SEQ ID NO: 2.

In addition to nucleotide sequences encoding conservative amino acid changes within the fundamental antifungal protein sequence, biologically functional equivalent nucleotide sequences of the present invention include nucleotide sequences containing other base substitutions, additions, or deletions. These include nucleic acids containing the same inherent genetic information as that contained in the DNA of SEQ ID NO: 1 or 4, and which encode peptides, polypeptides, or proteins conferring fungal resistance the same as or similar to that of SEQ ID NO: 2 upon host cells and organisms. Such nucleotide sequences can be referred to as "genetically equivalent modified forms" of the DNA shown in SEQ ID NO: 1 or 4 and can be identified by the methods described herein.

Mutations made in the cDNA, plasmid DNA, genomic DNA, synthetic DNA, or other nucleic acids encoding a antifungal protein of the invention, such as SEQ ID NO: 1, preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, it is not necessary that the nature of the mutations per se be predetermined. For example, in order to select for optimum characteristics of mutants at a given site, random mutagenesis can be conducted at the target codon. Alternatively, mutations can be introduced at particular loci by synthesizing oligonucleotides containing a mutant sequence, flanked by restriction sites enabling ligation to fragments of the native cDNA sequence. Following ligation, the resulting reconstructed nucleotide sequence encodes a derivative form of the nucleic acid sequence having the desired amino acid insertion, substitution, or deletion. In either case, the expressed mutants can be screened for desired antifungal activity by, for example, the method described in Example 4.

Specific examples of useful genetically equivalent modified forms of the DNA of SEQ ID NO: 1 or 4 include DNAs having a nucleotide sequence that exhibits a high level of sequence identity to SEQ ID NO: 1 or 4. This can range from about 70% or greater sequence identity, more preferably from about 80% or greater sequence identity, and most preferably from about 90% or greater sequence identity, to the DNA or corresponding moiety thereof of SEQ ID NO: 1 or 4.

Such genetically equivalent modified forms can be readily isolated using conventional DNA-DNA or DNA-RNA hybridization techniques or by amplification using polymerase chain reaction (PCR) methods. These forms should possess the ability to confer resistance to fungal pathogens when introduced by conventional transformation techniques into host cells normally sensitive to such pathogens.

The fragments and variants of the antifungal proteins, such as SEQ ID NO: 2, may be encoded by cDNA, plasmid DNA, genomic DNA, synthetic DNA, or mRNA. These nucleic acids should possess about 70% or greater sequence similarity, preferably about 80% or greater sequence similarity, and most preferably about 90% or greater sequence similarity, to corresponding regions or moieties of the DNA having the nucleotide sequence shown in SEQ ID NO: 1 or 4 or the mRNA corresponding thereto.

In the present invention, nucleic acids biologically functionally equivalent to the DNA having the nucleotide sequence shown in SEQ ID NO: 1 or 4 include:

DNAs having a length that has been altered either by natural or artificial mutations such as partial nucleotide deletion, insertion, addition, or the like, so that when the entire length of SEQ ID NO: 1 or 4 is taken as 100%, the biologically functional equivalent sequence has an approximate length of about 60% to about 120% of that of SEQ ID NO: 15, preferably about 80% to about 110% thereof; or Nucleotide sequences containing partial (usually about 20% or less, preferably about 10% or less, more preferably about 5% or less of the entire length) natural or artificial mutations so that such sequences code for different amino acids, but wherein the resulting polypeptide retains the antifungal activity of the antifungal polypeptides of this invention, such as SEQ ID NO: 2. The mutated DNAs created in this manner usually encode a polypeptide having about 70% or greater, preferably about 80% or greater, and more preferably about 90% or greater, sequence identity to the amino acid sequence of SEQ ID NO: 2.

In the present invention, the methods employed to create artificial mutations are not specifically limited, and such mutations can be produced by any of the means conventional in the art. Biologically functional equivalents to the DNA sequence disclosed herein produced by any of these methods can be selected for by assaying the peptide, polypeptide, or protein encoded thereby using the techniques described in the examples.

Due to the degeneracy of the genetic code, i.e., the existence of more than one codon for most of the amino acids naturally occurring in proteins, other DNA (and RNA) sequences that contain essentially the same genetic information as the DNA of the present invention and that encode substantially the same amino acid sequence as that encoded by the nucleotide sequence of SEQ ID NO: 1 or 4, can be used in practicing the present invention. This principle applies as well to any of the other nucleotide sequences discussed herein.

Biologically functional equivalent forms of the DNA of the present invention also include synthetic DNAs designed for enhanced expression in particular host cells. Host cells often display a preferred pattern of codon usage, and synthetic DNAs designed to enhance expression in a particular host should therefore reflect the pattern of codon usage in the host cell.

Other biologically functional equivalent forms of the DNA of SEQ ID NO: 1 or 4 useful in the present invention include those that have been modified to encode conjugates with other peptides, polypeptides, or proteins thereby encoding fusion products therewith.

Although one embodiment of a nucleotide sequence encoding a antifungal protein, such as SEQ ID NO: 2, is shown in SEQ ID NO: 1 or 4, it should be understood that the present invention also includes nucleotide sequences that hybridize to the sequence of SEQ ID NO: 1 or 4 and its complementary sequence, and that code for peptides, polypeptides, or proteins having the same or similar antifungal activity as that of the antifungal protein of the invention. Such nucleotide sequences preferably hybridize to SEQ ID NO: 1 or 4 or its complementary sequence under conditions of moderate to high stringency.

The nucleotide sequences described above are considered to possess a biological function substantially equivalent to that of the DNA of SEQ ID NO: 1 or 4 if they encode peptides, polypeptides, or proteins having an antifungal effect differing from that of SEQ ID NO: 2 by about 25% or less.

Vector and Host System

Another object of the invention is to provide an vector, containing the nucleic acid sequences as shown in SEQ ID NO: 1 or 4. In order to express a biologically active MAFP1, the nucleic acid sequences encoding MAFP1 or biologically functional equivalents, may be inserted into appropriate expression vector, i.e., a vector which contains the necessary elements for the transcription and translation of the inserted coding sequence. According to the invention, methods being well known to those skilled in the art may be used to construct expression vectors containing sequences encoding MAFP1 and appropriate transcriptional and translational control elements. These methods include in vitro recombinant DNA techniques, synthetic techniques, and in vivo genetic recombination. The vector is typically selected to be functional in the particular host cell employed (i.e., the vector is compatible with the host cell machinery such that amplification of the gene and/or expression of the gene can occur).

Another object of the invention is to provide a host cell transformed with the nucleic acid sequence as shown in SEQ ID No. 1 or 4 or the expression vector containing the sequence. According to the invention, a number of host systems may be utilized to contain and express sequences encoding MAFP1. These include, but are not limited to, microorganisms such as bacteria transformed with recombinant bacteriophage, plasmid, or cosmid DNA expression vectors; yeast transformed with yeast expression vectors; insect cell systems infected with virus expression vectors; plant cell systems transformed with virus expression vectors or with bacterial expression vectors; or animal cell systems. After the vector has been constructed and a nucleic acid sequence encoding MAFP1 has been inserted into the proper site of the vector, the completed vector may be inserted into a suitable host cell for amplification and/or polypeptide expression. The transformation of an expression vector for an MAFP1 protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. The host cell, when cultured under appropriate conditions, may synthesize an MAFP1 protein that can subsequently be collected from the culture medium (if the host cell secretes it into the medium) or directly from the host cell producing it (if it is not secreted). The selection of an appropriate host cell will depend upon various factors such as desired expression levels, polypeptide modifications that are desirable or necessary for activity (such as glycosylation or phosphorylation) and ease of folding into a biologically active molecule.

Utility

According to the invention, it is surprisingly found that the MAFP1 protein is a secretary protein and can effectively inhibit the growth of pathogenic fungi. Thus, the MAFP1 protein of the invention can be used in treating, controlling and/or preventing fungal diseases in animals, plants or microorganisms. The antifungal protein can be used directly by administering the antifungal protein to a subject or by transforming a subject with a vector comprising a DNA molecule encoding the antifungal protein to allow expression of the encoded antifungal protein in the subject to provide protection against fungal disease.

In addition to the use of the antifungal proteins of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14-nucleotide long contiguous sequence that has the same sequence as, or is complementary to, a 14-nucleotide long contiguous DNA segment of SEQ ID NO: 1 or 4 will find particular utility. Longer contiguous identical or complementary sequences, e.g., those of about 20, 30, 40, 50, 100, 200 bp, etc. (including all intermediate lengths and up to and including the full-length sequence of 409 basepairs) will also be of use in certain embodiments.

The ability of such nucleic acid primers to specifically amplify or hybridize to antifungal protein encoding sequences will enable them to be of use in detecting the presence of antifungal protein encoding sequences in a given sample. However, other uses are envisioned, including the use of the sequence information for the preparation of mutant species or primers for use in preparing other genetic constructions.

Antifungal Compositions

The invention also provides an antifungal composition comprising the antifungal protein of this invention, particularly for use in treating, controlling and/or preventing fungal diseases. The composition may contain suitable carriers, diluents, solvents, inert materials, or other additives, and optionally other antifungally active substances, excipients, auxiliaries, fertilizers or growth regulators.

The antifungal composition of the invention may be manufactured in a manner that is known in the art, e.g., by means of conventional methods comprising the steps of mixing, dissolving, granulating, dragee-making, levigating, emulsifying, encapsulating, entrapping, and/or lyophilizing steps.

The antifungal composition may be used for inhibiting the growth of or killing pathogenic fungi by administering to an animal by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means, or by applying the composition directly to the plant or plant environment such that the composition contacts the fungal pathogen using standard agricultural techniques (e.g., spraying or seed treatment).

As noted previously, the antifungal proteins of the present invention may be used in combination with other antifungal agents, including other peptides, polypeptides, and proteins that exhibit antifungal activity, so as to provide a broader spectrum of activity, i.e., to control additional pathogens or to provide multiple modes of action for the control of the same fungal pathogen.

Antifungal compositions contemplated herein also include those in the form of host cells, such as bacterial and fungal cells, that are capable of producing the present antifungal polypeptide.

Transgenic Organisms

The cDNA isolated in this manner may be transferred to an appropriate transformation/expression vector for introduction into a host cell. In yet another aspect, the antifungal gene of present invention can be used for producing a transgenic organism that expresses a nucleic acid segment encoding the novel antifungal protein of the present invention. The process of producing transgenic organisms is well known in the art such as by microinjection or by infection with a recombinant vector. In general, the method comprises transforming a suitable host cell with a DNA segment that contains a promoter operatively linked to a coding region that encodes an MAFP1 antifungal protein. Such a coding region is generally operatively linked to a transcription-terminating region, whereby the promoter is capable of driving the transcription of the coding region in the cell and, hence, providing the cell the ability to produce the recombinant protein in vivo.

The transgenic organisms may express a gene or gene segment encoding one or more of the novel antifungal proteins disclosed herein. By transforming a suitable host cell, such as a plant cell, with a recombinant nucleic acid sequence coding for an MAFP1 antifungal polypeptide such as SEQ ID NO: 2, the expression of the encoded antifungal protein can result in the formation of organisms exhibiting resistance to fungi. As used herein, the term "transgenic organism" is intended to refer to an organism that has incorporated DNA sequences, including but not limited to genes that are perhaps not normally present, DNA sequences not normally transcribed into RNA or translated into a protein ("expressed"), or any other genes or DNA sequences that one desires to introduce into the non-transformed organism, such as genes that may normally be present in the non-transformed organism but that one desires either to genetically engineer or to have altered expression.

More than one transgene will be incorporated into the genome of the transformed host plant cell. Such is the case when more than one MAFP1 antifungal protein-encoding DNA segment is incorporated into the genome of such an organism. In certain situations, it may be desirable to have one, two, three, four, or even more antifungal proteins (either native or recombinantly engineered) incorporated and stably expressed in the transformed transgenic organism.

It may also be desirable to incorporate other DNA segments into the genome of a transgenic organism, where such DNA encodes other antifungal proteins non-homologous to the disclosed antifungal proteins or various other proteins that improve the quality of products or performance of the organisms. Thus other types of proteins encoded by the DNA may include antibacterial, antiviral, or insecticidal proteins.

The transgenic organisms may be any convenient organisms, such as non-human mammal, plants or microorganisms, for example as used in laboratory test procedures such as rodents, e.g., mouse or rat; and for example as used for agricultures, such as rice, potato and tobacco. However, it will be obvious that the invention can be applied to every organism that is susceptible to a fungus towards which MAFP1 shows an inhibitory effect.

Primers

In certain embodiments, it is advantageous to use oligonucleotide primers. The sequence of such primers is designed for use in detecting, amplifying, or mutating a defined segment of an antifungal protein gene from using PCR technology. Primers for PCR and probes for hybridization screening can be designed based on the nucleotide sequence of the DNA shown in SEQ ID NO: 1 or 4. The primers should preferably not have self-complementary sequences nor have complementary sequences at their 3' ends in order to prevent dimer formation. The primers may contain restriction sites. The primers are annealed to the DNA and sufficient cycles of PCR are performed to yield a product readily visualized by gel electrophoresis and staining. The primers are generally at least 14 nucleotides in length, typically at least 20 nucleotides in length, preferably at least 24 nucleotides in length, and more preferably at least 28 nucleotides in length. Such primers will be capable of specifically priming genes encoding antifungal polypeptides or proteins having the same or similar antifungal activity as SEQ ID NO: 2. Segments of related antifungal protein genes from other species may also be amplified by PCR using such primers. The amplified fragments may be purified and inserted into an appropriate vector and propagated by conventional means known in the art.

The following examples are provided to aid those skilled in the art in practicing the present invention. Even so, the examples should not be construed to unduly limit the present invention as modifications and variations in the embodiments discussed herein may be made by those having ordinary skill in the art without departing from the spirit or scope of the present inventive discovery.

EXAMPLES

Materials

The *Monascus* strains used in the following Examples are selected from the *Monascus* Strains preserved in Bioresource Collection and Research Center (BCRC) in Taiwan: *M. pilo-* sus (BCRC 38072, BCRC 38093 and BCRC 31502), *M. barkeri* (BCRC 33309), *M. floridanus* (BCRC 33310), *M. lunisporas* (BCRC 33640), *M. ruber* (BCRC 31534, BCRC 31523, BCRC 31535, BCRC 33314, BCRC33323 and BCRC 31533), *M. kaoliang* BCRC 31506=CBS 302.78, *M. purpureus* (BCRC 31541=ATCC 16379, BCRC 33325=IFO 30873, BCRC 31615=DSM 1379, BCRC 31499=ATCC 16360=ATCC 26311 and BCRC 31542=ATCC 16365=ATCC 16426), and *M. sanguineus* BCRC 33446=ATCC 200613.

The fungal strains for testing the antifungal activities of *Monascus* strains or isolated and purified antifungal protein, MAFP1, are selected from *Helminthosporium panici* BCRC 35004 and *Paecilomyces variotii* BCRC 33174.

The fungal strains were inoculated on PDA (Potato Dextrose Agar, Difico Co.) culture plate and cultured at 25° C. for 7 to 14 days.

Example 1

The Distribution of the mafp1 Gene in *Monascus* Species

To discover if the mafp1 gene (SEQ ID NO: 1) exists in various *Monascus* species, primers for amplifying the mafp1 gene were designed using primer design software (Vector NTI (InforMax) Primer Design). The primers can be paired into 3 groups (1) primer H160-5F (SEQ ID NO: 6) and primer H160-3R (SEQ ID NO: 7), which can be used to amplify full-length sequence of the mafp1 gene; (2) primer H160-5S (SEQ ID NO: 8) and primer H160-3R, which can be used to amplify the nucleotide sequence encoding the sequence comprising the propeptide and the mature MAFP1 region; and (3) primer H160-5P (SEQ ID NO: 9) and primer H160-3R, which can be used to amplify the nucleotide sequence encoding the sequence comprising the mature MAFP1 region.

*Monascus* strains were cultured in YM media (7% glycerol, 3% of glucose, 3% of MSG (monosodium L-glutamate), 1.2% of polypetone, 0.2% of $NaNO_3$ and 0.1% $MgSO_4$-$7H_2O$, pH6.0) at 25° C. for 9 days. Fungus bodies and culture fluid were separated by vacuum filtration through 3M filter membrane. The Chromosomal DNA of the fungus was obtained by conventional phenol extraction method using suitable amount of fungus bodies.

PCR amplifications were conducted using the 3 primer pairs mentioned in the previous paragraph to exam the existence of the mafp1 gene in the *Monascus* species. 100 ng of chromosomal DNA obtained from *Monascus* strain were used as PCR template. The PCR reaction solution comprises 0.2 µl of 10 nM dNTP, 2.5 µl of 10×PCR buffer, 5 pmole forward primer and reverse primer, and 5 U Taq enzyme. The PCR conditions for amplifying the mafp1 gene are (1) 94° C. for 5 minutes; (2) 30 cycles of 94° C. for 40 seconds, 55° C. for 40 seconds and 72° C. for 30 seconds; (3) 72° C. for 3 minutes; and (4) maintain at 4° C. The PCR amplification results were shown in Table 1.

TABLE 1

PCR amplification examination of mafp1 gene in *Monascus* strains

| Strain | mafp1 gene[a] |
|---|---|
| *Monascus pilosus* BCRC 38072 | + |
| *Monascus pilosus* BCRC 38093 | + |
| *Monascus pilosus* BCRC 31502 | + |
| *Monascus ruber* BCRC 31523 | + |
| *Monascus ruber* BCRC 31533 | + |
| *Monascus ruber* BCRC 31534 | + |
| *Monascus ruber* BCRC 31535 | + |

TABLE 1-continued

PCR amplification examination of mafp1 gene in *Monascus* strains

| Strain | mafp1 gene[a] |
|---|---|
| *Monascus ruber* BCRC 33314 | + |
| *Monascus ruber* BCRC 33323 | + |
| *Monascus barkeri* BCRC 33309 | + |
| *Monascus floridanus* BCRC 33310 | + |
| *Monascus lunisporas* BCRC 33640 | + |
| *Monascus kaoliang* BCRC 31506 | − |
| *Monascus purpureus* BCRC 31542 | − |
| *Monascus purpureus* BCRC 31499 | − |
| *Monascus purpureus* BCRC 31541 | − |
| *Monascus purpureus* BCRC 31615 | − |
| *Monascus purpureus* BCRC 33325 | − |
| *Monascus sanguineus* BCRC 33446 | − |

[a]"+" denotes that all three primer pairs can be used to amplify the mafp1 gene segments; "−" denotes that all three primer pairs cannot be used to amplify the mafp1 gene segments.

The results showed that the mafp1 gene exists in *M. barkeri* BCRC 33309, *M. floridanus* BCRC 33310, *M. lunisporas* BCRC 33640, *M. pilosus* (BCRC 38072, BCRC 38093 and BCRC 31502) and *M. ruber* (BCRC 31523, BCRC 31533, BCRC 31534, BCRC 31535, BCRC 33314 and BCRC 33323). There is no mafp1 gene found in *M. kaoliang* BCRC 31506, *M. purpureus* (BCRC 31499, BCRC 31542, BCRC 31541, BCRC 31615 and BCRC 33325) and *M. sanguineus* BCRC 33446. It is suggested that the *Monuscus* species such as *M. barkeri*, *M. floridanus*, *M. lunisporas*, *M. pilosus* and *M. ruber* may have antifungal activities.

Example 2

Sequence Comparison of the mafp1 Gene of cDNA Thereof in Various *Monascus* Species Cloning and Sequencing of the mafp1 Gene

*Monascus* strains were cultured in YM media (7% glycerol, 3% of glucose, 3% of MSG (monosodium L-glutamate), 1.2% of polypetone, 0.2% of $NaNO_3$ and 0.1% $MgSO_4$-$7H_2O$, pH6.0) at 25° C. for 9 days. Fungus bodies and culture fluid were separated by vacuum filtration through 3M filter membrane. The Chromosomal DNA of the fungus was obtained by conventional phenol extraction method using suitable amount of fungus bodies. PCR amplifications were conducted using primers of H160-5F and H160-3R. 100 ng of chromosomal DNA obtained from *Monascus* strain were used as PCR template. The PCR reaction solution comprises 0.211 of 10 nM dNTP, 2.5 µl of 10×PCR buffer, 5 pmole forward primer and reverse primer, and 5 U Taq enzyme. The PCT conditions for amplifying the mafp1 gene are (1) 94° C. for 5 minutes; (2) 30 cycles of 94° C. for 40 seconds, 55° C. for 40 seconds and 70° C. for 30 seconds; (3) 72° C. for 3 minutes; and (4) maintain at 4° C. The PCR amplified nucleotide fragments of full-length sequence of mafp1 gene were purified and cloned into pGEM-T vector (Promega). The plasmid DNA was extracted for sequencing.

Cloning and Sequencing of the mafp1 cDNA

*Monascus* strains were cultured in YM media (7% glycerol, 3% of glucose, 3% of MSG (monosodium L-glutamate), 1.2% of polypetone, 0.2% of $NaNO_3$ and 0.1% $MgSO_4$-$7H_2O$, pH6.0) at 25° C. for 9 days. Fungus bodies and culture fluid were separated by vacuum filtration through 3M filter membrane. Total RNA of the fungus was obtained by RiboPure™-yeast kit (Ambion) using suitable amount of fungus bodies. Improm-II™ Reverse Transcription system kit (Promega) was used to prepare the first strand cDNA. Specific primer pair (H160-5F and H160-3R) of mafp1 gene was used to in PCR to amplify the full-length mafp1 cDNA fragments. Suitable amount of the first strand cDNA was used as the PCR template. The PCR reaction solution comprises 0.2 µl of 10 nM dNTP, 2.5 µl of 10×PCR buffer, 5 pmole H160-5F and H160-3R, and 5 U Taq enzyme. The PCT conditions for amplifying the mafp1 cDNA are (1) 94° C. for 5 minutes; (2) 30 cycles of 94° C. for 40 seconds, 55° C. for 40 seconds and 72° C. for 1 minute; (3) 72° C. for 3 minutes; and (4) maintain at 4° C. The amplified PCR products were purified and cloned into pGEM-T vector (Promega). The plasmid DNA was extracted for sequencing.

The results of the sequence comparison of the mafp1 gene of cDNA thereof in various *Monascus* species were shown in Table 2.

TABLE 2

Sequence similarity analysis of mafp1 gene and cDNA thereof in *Monascus* species

| Similarity (%) | *Monascus pilosus* BCRC 38072 | *Monascus pilosus* BCRC 38093 | *Monascus pilosus* BCRC 31502 | *Monascus ruber* BCRC 31533 |
|---|---|---|---|---|
| *Monascus pilosus* BCRC 38072 | 100 | 100 | 100 | 100 |
| *Monascus pilosus* BCRC 38093 |  | 100 | 100 | 100 |
| *Monascus pilosus* BCRC 31502 |  |  | 100 | 100 |
| *Monascus ruber* BCRC 31533 |  |  |  | 100 |

The results showed that the sequences of the mafp1 gene and cDNA thereof in *Monascus pilosus* BCRC 38093, *Monascus pilosus* BCRC 31502 and *Monascus ruber* BCRC 31533 have 100% sequence similarity to which of *Monascus pilosus* BCRC 38072. It is proved that all these *Monascus* strains have the same mafp1 gene, and the transcribed mRNAs are the same. It is concluded that these strains can produce the same MAFP1 protein.

Example 3

Pathogen Dual Culture Assay

To confirm the antifungal activity of *Monascus* fungi, round fungal blocks (in 0.5 cm diameter) of two *Monascus* species (*M. pilosus* BCRC 38072 and BCRC 38093) and pathogenic fungus (*H. panici* BCRC 35004) were placed on two side of a PDA plate cultured at 28° C. The growth inhibitions of the pathogenic fungus were observed. The preliminary results showed that both strains can inhibit the growth of *H. panici* BCRC 35004.

*M. pilosus* BCRC 38093 is a mutant of *M. pilosus* BCRC 38072. They have the same mafp1 sequence (as shown in Table 2) and have the same antifungal activity. *M. pilosus* BCRC 38093 was used in the following purification example.

Example 4

Purification of *Monascus* Antifungal Protein (MAFP1), N-Terminal Sequencing, and Antifungal Activity Assay Purification of MAFP1

400 ml of *M. pilosus* BCRC 38093 culture broth, after cultured at 25° C. for 9 days, were separated using centrifugation under 4,500 rpm with 0.22 µm filter membrane to remove the impurities. 30 kDa filter membrane was used to process the centrifuged broth, and solution containing molecules smaller than 30 kDa were collected and adjust to pH6.6. Mixing 10 ml of CM Sepharose Fast Flow (Amersham Biosciences) resin with 40 ml protein solution at room temperature for 16 hours. The mixtures were packed into empty chromatography column. Unbound proteins were washed out. The column was eluted in 100 ml solution A (25 mM NaCl in 10 mM Na-phosphate buffer, pH6.6) and solutions with different ratios of solution A and solution B (1M NaCl in 10 mM Na-phosphate buffer, pH6.6) were used to elute the proteins. The concentration gradients of solution A were from 95%, 80%, 75%, 50% to 0%. 100 ml solutions were used for each gradient, and the eluted fractions were divided into 15 ml test tubes, separately.

1 ml of solutions from each test tube were precipitated with TCA and analyzed by SDS-PAGE. The molecular weight of the MAFP1 protein is about 7 kDa. Solutions containing MAFP1 protein were pooled into one test tube. The solutions were centrifuged under low speed (2,000 rpm) with 3 kDa filter membrane. Solutions containing protein larger than 3 kDa were collected and concentrated and de-salted with 1 kDa filter membrane. The purified MAFP1 protein is used in the pathogen antagonistic assay and protein N-terminal sequencing.

N-Terminal Sequencing

Figure 3:
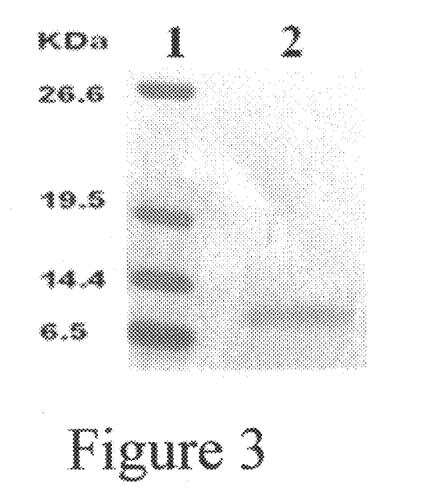
FIG. 3 shows the SFDS PAGE analysis of purified *Monascus* antifungal protein MAFP1. Lane 1: protein marker; lane 2: purified MAFP1 protein.

The purified MAFP1 solution was precipitated with TCA and analysis using 15% acrylamide SDS-PAGE. Different concentrations of lysozyme were used as protein quantitative reference. After the electrophoresis, the proteins were transferred from the gel to PVDF membrane and stained with 0.1% Coomassie Brilliant Blue R250 (see FIG. 3). The MAFP1 protein band was cut out and de-colored with methanol. The membrane was wash several times with ddH$_2$O and dried in dark place. The treated MAFP1 protein was N-terminal sequenced using Applied Biosystems Procise Sequencer 494.

The N-terminal sequencing results of purified MAFP1 protein showed that the N-terminal of the purified MAFP1 protein is LSKYGGECSLQHNTC (SEQ ID NO: 5). The N-terminal sequence of the purified protein is consistent with the first 15 amino acid sequence of the mature form of MAFP1 protein (SEQ ID NO: 3). It is proved that the purified protein is the mature form MAFP1 protein.

Antifungal Activity Assay

Figure 4:
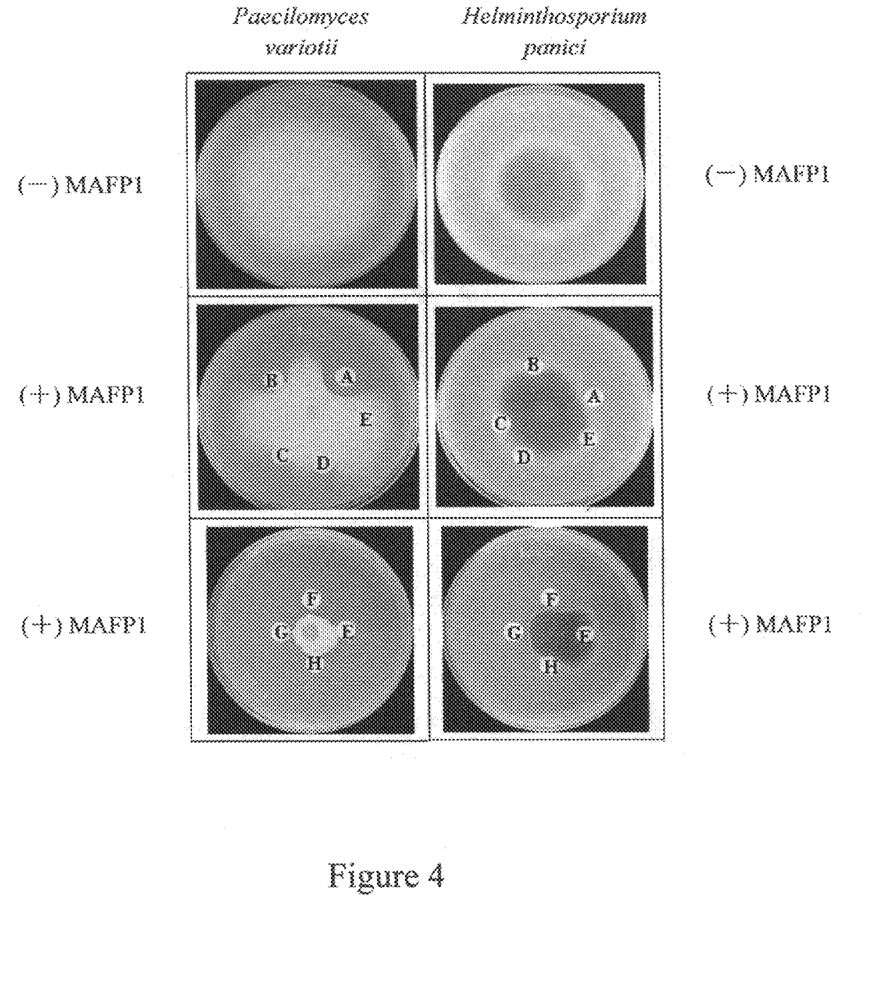
FIG. 4 shows the antifungal activity assay of *Monascus* antifungal protein MAFP1. The antifungal ability of purified MAFP1 protein against pathogenic fungi *Paecilomyces variotii* (BCRC 33174) and *Helminthosporium panici* (BCRC 35004) was studied by dual culture and the growth of fungus was observed. (−)MAFP1: control groups without MAFP1; (+)MAFP1: experiment groups with different amount of MAFP1 protein. A to H individually represents paper discs with 0.4 μg, 0.2 μg, 0.1 μg, 0.05 μg, 0 μg, 0.8 μg, 0.64 μg, and 0.32 μg of MAFP1 protein.

Pathogen antagonistic dosage assays were conducted to confirm the antifungal activity of the purified MAFP1 protein. Fungal blocks of pathogenic fungi (*P. variotii* BCRC 33174 and H. panici BCRC 35004) were place in the center of PDA plates. 6 mm paper discs with different concentrations of MAFP1 solutions (containing 0 to 0.8 μg of purified MAFP1 protein) were placed surround the fungal block of pathogenic fungus. The plates were cultured at 28° C. and the growth inhibitions of the pathogenic fungi were observed. The results were shown in FIG. 4. The results showed that 0.2 μg of MAFP1 protein can significantly inhibit the growth of P. variotii. The results also showed that 0.4 μg of MAFP1 protein can significantly inhibit the growth of H. panici. It is observed that the higher the MAFP1 concentration, the stronger the inhibitory activity to the growth pathogenic fungus. It is proved that the MAFP1 protein from Monascus species is a protein having antifungal activity, which can inhibit the growth of human pathogen, such as P. variotii, and plant pathogen, such as H. panici.

The invention claimed is:

1. An isolated and purified antifungal protein comprising the amino acid sequence of SEQ ID NO: 3.

2. A composition comprising the antifungal protein of claim 1, and a suitable carrier, wherein the protein is present in an amount sufficient to inhibit fungal growth.

3. The composition of claim 2, which comprises an additional antifungal agent.

* * * * *